(12) United States Patent
Chau et al.

(10) Patent No.: US 8,545,449 B2
(45) Date of Patent: Oct. 1, 2013

(54) MULTI-PORT FLUID ACCESS DEVICE AND METHOD

(75) Inventors: Christopher Yim Chau, Pharr, TX (US); Jose Antonio Badillo, Hidalgo, TX (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 658 days.

(21) Appl. No.: 12/456,756

(22) Filed: Jun. 22, 2009

(65) Prior Publication Data

US 2010/0324466 A1 Dec. 23, 2010

(51) Int. Cl.
*A61M 5/178* (2006.01)
*A61M 37/00* (2006.01)

(52) U.S. Cl.
USPC .................................. 604/164.08; 604/6.16

(58) Field of Classification Search
USPC ............... 604/6.1, 6.16, 164.08, 244–249, 604/256, 284, 288.01–288.04, 533
See application file for complete search history.

(56) References Cited

U.S. PATENT DOCUMENTS

| | | | |
|---|---|---|---|
| 5,147,321 A | 9/1992 | Slonina et al. | |
| 5,322,516 A | 6/1994 | Brugger | |
| 5,372,143 A | 12/1994 | Bernes et al. | |
| 5,743,894 A | 4/1998 | Swisher | |
| 5,876,366 A | 3/1999 | Dykstra et al. | |
| 6,290,682 B1 * | 9/2001 | Myers | 604/247 |
| 7,867,204 B2 * | 1/2011 | Bartholomew et al. | 604/249 |
| 2006/0217671 A1 * | 9/2006 | Peppel | 604/246 |
| 2007/0093762 A1 * | 4/2007 | Utterberg et al. | 604/256 |

* cited by examiner

*Primary Examiner* — Philip R Wiest
(74) *Attorney, Agent, or Firm* — Hamilton, Brook, Smith & Reynolds, P.C.

(57) ABSTRACT

The invention provides a multi-port fluid access device for medical use, such as in a blood-flow circuit during dialysis. The device has a main tubular body and a needle access port and a needleless access port located at positions axially offset from each other. Each port has a tubular body with a septum sealing the passageway to the main fluid channel of the main tubular body. Alongside the main tubular body are members providing finger-gripping surfaces at or near the axial position of the needle access port. There is also a needle shield located between the finger gripping surfaces and the needle access port. Use of the device permits either or both of needle access and needleless access to a patient's blood during dialysis.

16 Claims, 4 Drawing Sheets

MULTI-PORT FLUID ACCESS DEVICE AND METHOD

FIELD OF THE INVENTION

The present invention relates generally to apparatus and methods for providing access to fluid flows in medical procedures, such as hemodialysis, including use of a manifold having injection/administration port structures for the introduction of required drugs or other additives or for withdrawal of fluids from a patient, and, in particular, to a manifold having multiple injection/administration ports for use with extracorporeal blood circuit tubing.

BACKGROUND OF THE INVENTION

Many medical patients suffering from kidney disease are treated with a dialysis machine to cleanse their blood. A dialysis machine typically includes a blood pump and an extracorporeal blood circuit. Arterial blood is drawn from a patient's body, passes through the dialysis unit and dialyzed blood is returned to the patient's venous system. The extracorporeal blood circuit, which includes a length of extracorporeal blood circuit tubing several feet long at each end, may connect to the patient's arterial and venous systems directly via a large bore dialysis needle, or via separate dialysis access devices. The access devices each include a shorter tubular section, adapted at one end for connecting to an open end of the extracorporeal blood circuit tubing, and at the other end having a large bore dialysis needle for accessing the patient's arterial or venous blood.

Either or both of the extracorporeal blood circuit tubing and the access devices may include flow shut-off clamps and fluid access devices that have injection/administration port structures. The port structures provide mechanisms through which a dialysis administrator can, for example, safely access the arterial or venous blood flow to remove samples of the patient's blood or inject drugs or fluids. Some injection/administration ports are adapted for use with a needle syringe, while others are adapted to provide needleless syringe access with a Luer-type connection. The needleless access ports have a pressure-responsive structure or mechanism that opens the port upon pressure applied by a syringe tip.

It is desirable that the fluid access devices be safe and easy to use. It is also desirable that a fluid access device be low-cost, while still providing flexibility of use.

SUMMARY OF THE INVENTION

The invention, in one aspect, provides a multi-port fluid access device forming a rigid plastic fluid manifold, that has a main tubular body providing a central flow channel, a first open end, a second open end, and connection structure adapted for connecting to blood-flow tubing at each end. The device has a needle accessible first fluid port at a first axial position along the tubular section. The first fluid port has a tubular body extending from the main tubular section. Inside the tubular body of the first fluid port is a septum adapted for needle penetration to provide needle access to the central flow channel. The device additionally has a needleless access second fluid port at a second axial position along the tubular section that is offset from the first axial position. The second fluid port also has a tubular body extending from the main tubular section, the distal end of which preferably includes a Luer-type fitting adapted for rotational engagement with a mating Luer fitting. The second port also has pressure-responsive structure, including a second septum, within its tubular section that is adapted to allow needleless fluid coupling between the central flow channel and a syringe connected with the mating Luer fitting when the Luer-type fitting is engaged by the mating Luer fitting. Preferably the Luer-type fitting is a female Luer fitting, and the mating Luer fitting is a male Luer fitting. The first and second septa are formed of materials that permit expansion under compression.

The device includes gripping members that provide gripping surfaces. The gripping members are located at or near the first axial position and extend in a direction generally opposite from the first fluid port. The gripping surfaces are preferably uneven or rough surfaces to enhance finger gripping. There is also a protective flange, or needle shield, positioned between the first port and the gripping surfaces, having a surface extending outward from the tubular section and from the axis of the first port. This serves to protect the fingers of a person holding the fluid manifold by the gripping surfaces from being pierced by a needle that misses the first fluid port.

In one embodiment, the needle shield is offset from a plane extending through the axis of the main tubular body. In another embodiment, the needle shield extends approximately radially outward from opposite sides of the main tubular body, and the gripping members are on a side of the needle shield opposite from the first fluid port (i.e., near the second fluid port). In yet another embodiment, the device includes a second set of gripping members located at or near the second axial position and on the other side of the needle shield (i.e., near the first fluid port). In this embodiment, a medical provider would hold the device by the second set of gripping members when coupling or decoupling a mating Luer fitting with the second fluid port.

In a preferred embodiment, the multi-port fluid access has one needle access fluid port and one needleless fluid access port. The central axes of the short tubular sections of the first and second fluid ports are parallel to each other and transverse to the central axis of the main tubular section, with their open ends on opposite sides of the main tubular section. In some embodiments, the tubular sections of the first and second fluid ports have axes that are transverse to the central axis of the main tubular section, but are not parallel to each other. In still other embodiments, one or both of their axes' may form an acute angle with the main tubular section's central axis. However, in all embodiments the first and second fluid ports are positioned and structured such that a needle can be inserted through the septum of the first fluid port without contacting or interfering with the pressure-responsive structure of the second fluid port.

In another embodiment, the multi-port fluid access device has one needle access fluid port and two needleless access fluid ports that are offset axially along the main tubular body from the needle access fluid port.

In yet another embodiment, the multi-port fluid access device is marked or color-coded for particular uses. For example, a red-colored device may be connected to blood-flow tubing receiving blood from a patient's arterial system, and a blue-colored device may be connected to blood-flow tubing connected to the patient's venous system. Other markings or colors may be utilized for other applications.

In another aspect, the invention provides a method of performing dialysis. The method utilizes a dialysis machine and extracorporeal blood-flow tubing adapted for the passage of blood from and to a dialysis patient through the dialysis machine. The method includes providing a blood flow circuit from a patient's arterial system through a section of extracorporeal blood-flow tubing, through a dialysis machine, and from the dialysis machine through a second section of blood-flow tubing to the patient's venous system, and providing a multi-port fluid access device as described above connecting between two segments of such tubing. The method further includes flowing the patient's blood through the blood flow circuit and dialyzing the blood with the dialysis machine, finger gripping the fluid access device by the gripping surfaces, inserting a first syringe needle through the septum of the first fluid port and passing a fluid through the first needle. Alternatively, the method, instead of inserting a syringe needle through the septum of the first fluid port, includes connecting a mating Luer fitting to the Luer-type fitting of the second fluid port such that a syringe connected with the mating Luer fitting applies pressure to pressure-responsive structure within the second fluid port to open the second fluid port, and passing a fluid through the second fluid port between the syringe and central fluid channel. The fluid that is passed through either fluid port may be the patient's blood, e.g. for sampling, or may be a fluid injected into the blood, e.g. a drug or supplement, a saline or nutrient solution, additional blood, a blood component or components, or a blood substitute.

In another embodiment, such fluid connections are made through both the first and second fluid fittings, and the method includes passing a first fluid through the first fluid port and passing a second fluid through the second fluid port. The two fluid ports may be engaged during overlapping time periods, and the two fluids may be passed at the same time or at different times during the patient's dialysis treatment. Passing the fluids can take place at any time during the patient's dialysis treatment.

There are several advantages to the invention. The device of the invention includes two different types of fluid access ports in a single unit, providing an inexpensive yet flexible piece of medical equipment. This reduces the need to stock separate fluid access ports. Because multiple fluid ports are included in a single device, it reduces the need to use multiple devices. The device provides both needle fluid access and needleless fluid access. The different types of fluid access ports are offset from each other, so that a needle inserted through the needle access fluid port will not interfere with the pressure responsive structure of the needleless fluid port(s). Using this device, multiple fluids can advantageously be injected into the blood flow circuit at essentially the same location and the same time. Distinctly marked or colored devices can advantageously be used for different applications. The device also has attractive and useful safety features, such as the finger gripping surfaces, and the protective flange.

Other objectives and advantages of the invention will become more apparent from the following detailed description when taken in conjunction with the accompanying drawings.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
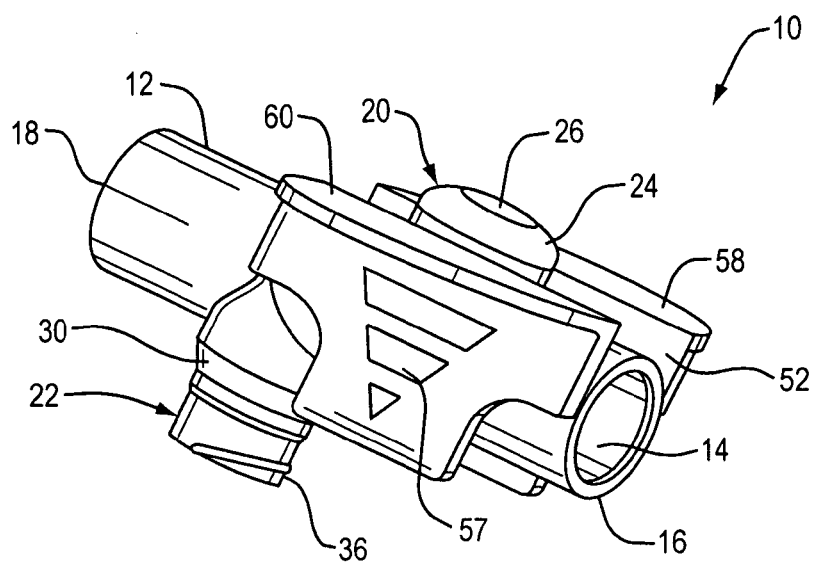
FIG. 1 is a perspective view of a first embodiment of a multi-port fluid access device of the invention.

A description of example embodiments of the invention follows.

The invention provides convenient, low-cost multi-port fluid access device that can be advantageously used in blood dialysis procedures. A single structure provides two different types of fluid access to a patient's blood flow during dialysis: through a first fluid port via a syringe needle; and needleless access through a second fluid port, e.g., via a Luer-type fitting and syringe.

Referring now to FIGS. 1-4, a dual-port fluid access device 10 is formed of unitary piece of molded rigid plastic suitable for sterile medical use. It includes a straight main tubular body 12 that has a central flow channel 14 which is open at first and second ends 16, 18. On one side of the main tubular body 12 closest to the first end 16 is a first fluid port 20. On the other side of the main tubular body 12 there is a second fluid port 22, which is offset from the first fluid port 20 along the length of the main tubular body 12 and positioned closer to the second end 18. The first fluid port provides needle fluid access, and the second fluid port provides needleless fluid access.

The first fluid port 20 has a short first tubular body 24 having a first fluid passageway 26 that connects to the central channel 14. A septum 28 seals the first fluid port's fluid passageway 26. The first fluid port 20 is intended to be accessed with a syringe needle (metal or plastic), which can penetrate the septum 28 to draw blood from the central flow channel 14 or to administer drugs or fluids into the blood flow. Septum 28 is made of an elastic or soft plastic material, as is generally known in the art, to permit expansion under compression. Septum 28 may be a split septum to make needle penetration easier.

The second fluid port 22 in the exemplary embodiment depicted in FIGS. 1-4 has a short second tubular body 30 having a second fluid passageway 32 that connects to the central fluid channel 14. A pressure-responsive structure or mechanism 34 seals the fluid passageway 32. The outer distal surface of the tubular body 30 forms a female Luer-type fitting 36. When rotationally engaged with a mating male Luer fitting (not illustrated), a tip of a syringe that is coupled with the male Luer fitting pushes against the pressure responsive structure 34 to open the fluid passageway 32. In a preferred embodiment, male and female Luer fittings comply with ISO 594/1 and 594/2, respectively.

Figure 2:
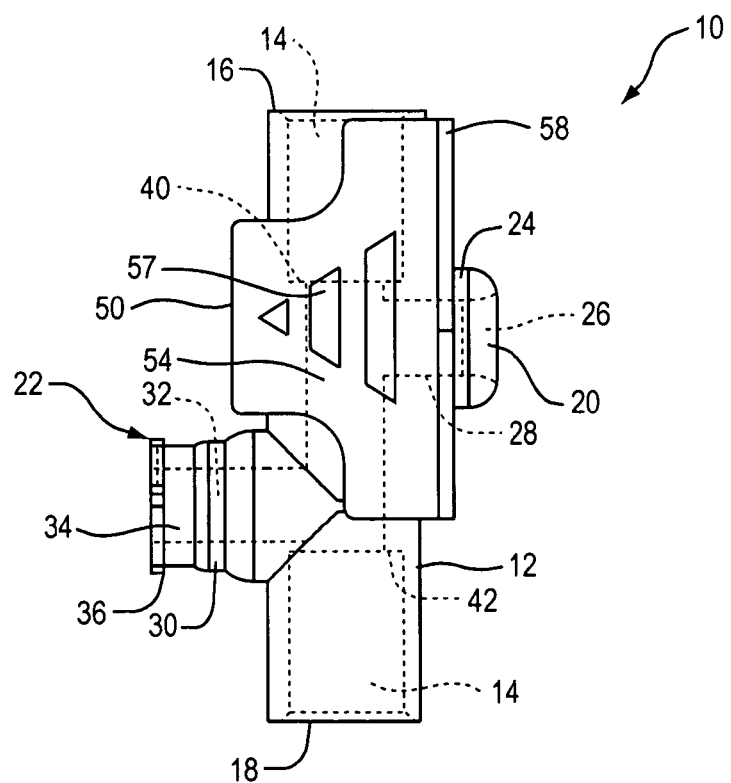
FIG. 2 is a side view of the first embodiment, showing internal passageways in hidden lines.
Figure 3:
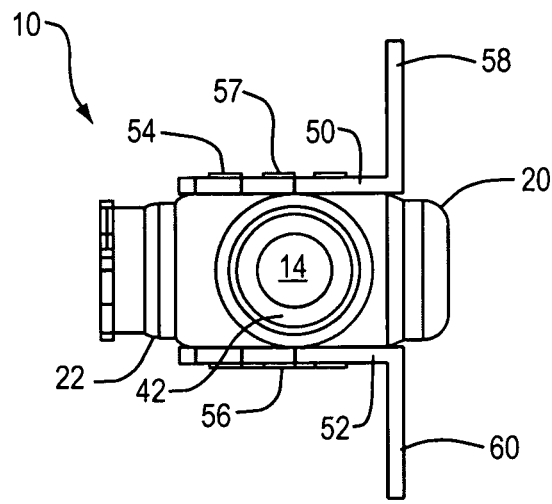
FIG. 3 is a left end view of the device of FIG. 2.
Figure 4:
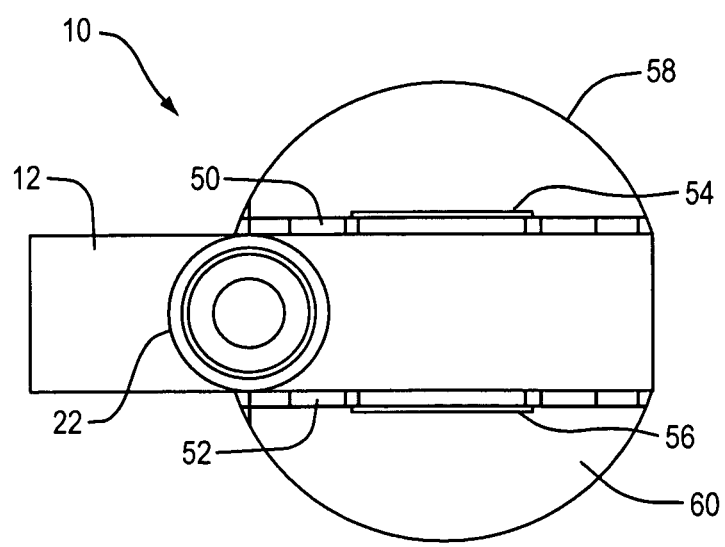
FIG. 4 is a bottom view of the device of FIG. 2.

Medical tubing (not shown) can be inserted into each end 16, 18 of the central flow channel 14. Fluid can flow through the central flow channel 14 in either direction, and can be under positive or negative pressure. To prevent the medical tubing from passing too far into the central flow channel 14 and interfering with fluid flow through the first and second fluid ports 20, 22, the inner surface of the main tubular body 12 forms a first shoulder 40 nearest to the first end 16 and a second shoulder 42 nearer to the second end 18. As best shown in FIG. 2, the first shoulder 40 is positioned so that the medical tubing inserted into the first end 16 will stop just short of the central passageway 26 of the first fluid port 20. Similarly, the second shoulder 42 is positioned so that medical tubing inserted into the second end 18 will stop short of the fluid passageway 32 of the second fluid port 22.

In the illustrated embodiment, the main tubular body 12 is approximately 1.4 inches (35.8 mm) long. The first and second fluid ports 20, 22 are centered about 0.46 inches (11.8 mm) from first and second ends 16, 18, respectively, and about 0.39 inches (9.5 mm) from each other. The inner diameter of the central flow channel 14, from the ends 16, 18 up to the shoulders 40, 42, respectively, is sized to fit standard 0.265 inch (6.73 mm) OD medical tubing. The inner diameter of the main tubular body 12 between the shoulders 40, 42 is approximately 0.17 inch (4.4 mm). The fluid passageways 26, 32 of the first and second fluid ports 20, 22 where they connect to the central flow channel 14 are approximately the same diameter as that of the central flow channel 14.

Positioned on opposite sides of the main tubular body 12 and centered at the axial location of the first fluid port are two members 50, 52. Members 50, 52 provide substantially flat, parallel finger-gripping surfaces 54, 56, respectively. Preferably, gripping surfaces 54, 56 are textured, rather than smooth, to enhance friction for gripping. Surfaces 54, 56 may also include raised or indented structures to further improve gripping. As illustrated, these structures may be in the form of bars 57, although other structures and designs can be used as well. The fingers of a person holding the device 10 by the gripping surfaces 54, 56 will not be interfered with by a fluid line connected to the second fluid port 22 because of the offset between the first fluid port 20 and the second fluid port 22.

Device 10 also includes a needle shield. Projecting outward from the members 50, 52 at their ends closest to the first fluid port are respective plates 58, 60, or flanges. The plates 58, 60 provide a safety barrier between the finger-gripping surfaces 54, 56 and the first fluid port 20 to prevent accidental slippage of a needle being inserted through the first fluid port 20 from puncturing the fingers or hand of a person holding the device by the gripping surfaces 54, 56. In the illustrated embodiment, plates 58, 60 have rounded edged with a radius of about 0.45 inches (11.4 mm). Alternatively, the needle shield may be rectangular shaped or any other suitable shape, or larger or smaller.

The dual-port fluid access device 10 can be used in conjunction with blood dialysis. Dual-port fluid access device 10 may be connected between any two sections of blood flow tubing used in dialysis treatment. It may be used with tubing connecting the patient's arterial flow to the dialysis machine, or with tubing connecting dialyzed blood flowing from the dialysis machine to the patient's venous system. It may be connected between segments of extracorporeal blood flow tubing, or between such tubing and the tubing of a dialysis access device. Either of fluid ports 20, 22 may be used to remove blood samples or to administer/inject fluid substances to the blood flow, e.g. drugs, saline or other electrolyte solutions, sucrose or other nutrient solutions, transfused blood, plasma, or other blood components, blood substitutes, or any other fluid that may need to be administered.

The dual-port fluid access device of the invention is not restricted to use in dialysis treatment. It may be used in a fluid line for other medical purposes and in conjunction with a flow of other fluids besides human blood.

The first fluid port 20 and the second fluid port 22 may be used to access a fluid flow through the central flow channel 14 singly, serially, or at the same time or overlapping times.

The dual-port fluid access device can be a red or pink color for use on the arterial side of a patient's blood flow, and blue or purple colored for use on the venous flow side. Other colors or distinctive markings (not shown) may be used for other special purposes.

Figure 5:
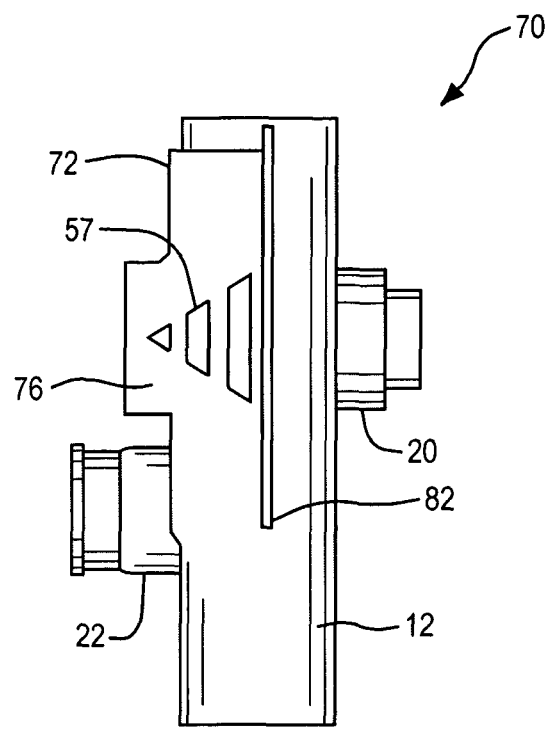
FIG. 5 is a side view of a second embodiment of a device of the invention.
Figure 6:
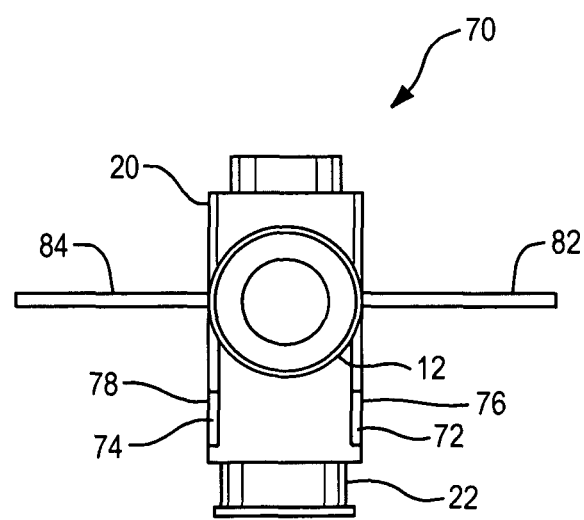
FIG. 6 is an end view of the device of FIG. 5.

FIGS. 5 and 6 illustrate a second embodiment of a dual-port fluid access device 70. In this embodiment, members 72, 74 providing finger-gripping surfaces 76, 78 are set below the mid-line (diagonal) of the main tubular body 12, and needle-shield plates 82, 84 project outward from a center-line of the main tubular body 12.

Figure 7:
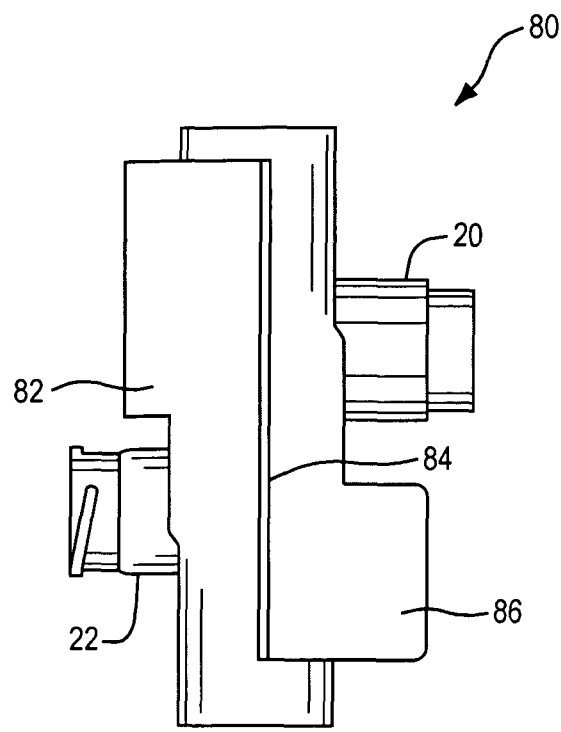
FIG. 7 is a side view of a third embodiment of a device according to the invention.

FIG. 7 illustrates another embodiment of a dual-port fluid access device 80. This device has a first pair of finger gripping surfaces 82 (only one shown) located on one side of the finger shield 84 near the second fluid port 22 and opposite the first fluid port 20, and a second set of gripping surfaces (only one shown) 86 located on the opposite side of the finger shield 84 near the first fluid port 20 and opposite the second fluid port 22. The second set of finger gripping surfaces 86 allow a provider to have a secure grip on the device when making a connection with the needleless second fluid port 22.

In other embodiments, the first and second fluid ports 20, 22 are less than 180 degrees apart. It is possible for the tubular body of the first fluid port and/or the second fluid port to be oriented at an acute angle, rather than perpendicular to the main tubular body, provided that, under such circumstances, they are positioned and oriented such that a needle penetrating through the first fluid port does not interfere with the pressure-responsive structure within the second fluid port.

Figure 8:
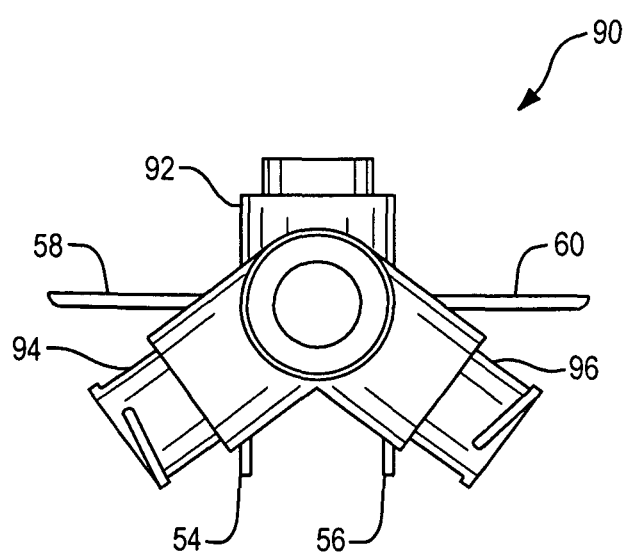
FIG. 8 is an end view of a fourth embodiment of a device according to the invention.

Illustrated in FIG. 8 is an embodiment of a multi-port fluid access device 90 that has one needle access fluid port 92 and two needleless access fluid ports 94, 96. The needleless access fluid ports 94, 96 are at the same axial position, which is offset from the axial position of the needle access fluid port 92. The two needleless access fluid ports 94, 96 are each 120 degrees apart from the needle access port 92 and from each other. This embodiment of the invention can provide even greater flexibility of use than dual-port embodiments.

While the needleless access fluid ports of the specific embodiments described and illustrated herein all include a Luer-type fitting, other types of needleless access port structures may be used if medically appropriate.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

While this invention has been particularly shown and described with references to example embodiments thereof, it will be understood by those skilled in the art that various changes in form and details may be made therein without departing from the scope of the invention encompassed by the appended claims.

What is claimed is:

1. A multi-port fluid access device forming a rigid plastic fluid manifold, comprising:

a straight main tubular body extending longitudinally and having an inner surface forming a central flow channel, a first open end, and a second open end, wherein the inner surface forms a connection structure adapted for connecting to blood-flow tubing at each end of the tubular body;

a needle access first fluid port at a first axial position along the main tubular body, the needle access first fluid port comprising a first tubular body connecting to the main tubular body, and a first septum within the first tubular body adapted for needle penetration to provide needle access to the central flow channel;

a needleless access second fluid port at a second axial position along the tubular section that is offset from the first axial position, the needleless access second fluid port comprising a second tubular body connecting to the main tubular body;

gripping members centered at the first axial position and on opposite sides of the main tubular body, the gripping members comprising respective gripping surfaces; and a needle shield, projecting outwardly from and positioned between the first fluid port and the gripping surfaces, the needle shield adapted to prevent a needle from puncturing a finger of a user holding the device by the gripping surfaces.

2. The device of claim 1, wherein the distal end of the second tubular body includes a fitting adapted for engagement with a mating fitting, and pressure-responsive structure, including a second septum, within the second tubular body that is adapted to allow needleless fluid coupling between the central flow channel and a syringe connected with the mating fitting when the fitting is engaged by the mating fitting.

3. The device of claim 2, wherein the fitting is a Luer fitting.

4. The device of claim 3, wherein the Luer fitting is a female Luer fitting.

5. The device of claim 1, wherein the needle access first fluid port and the needleless access second fluid ports have respective first and second axes that are transverse to the central flow channel.

6. The device of claim 5, wherein the first and second axes are coplanar.

7. The device of claim 1, wherein the connection structure includes a first annular shoulder at an axial position between a first end and a central passageway of the needle access first fluid port.

8. The device of claim 7, wherein the connection structure further includes a second annular shoulder at an axial position between a second end and a central passageway of the needleless access second fluid port.

9. The device of claim 1, wherein the gripping surfaces include an uneven surface to enhance gripping.

10. The device of claim 1, wherein the gripping surfaces include two substantially parallel spaced planar members positioned on opposite sides of the tubular section, wherein the protective flange is oriented perpendicular to the spaced planar members.

11. The device of claim 1, wherein the needle shield includes plates on opposite sides of the main tubular section.

12. The device of claim 1, further comprising a needleless access third fluid port, including a third tubular body at an axial position of the main tubular body that is offset from the first axial position.

13. The device of claim 12, wherein the second and third fluid ports are at the same axial position and rotational offset from each other and the first fluid port with respect to the central axis of the main tubular body.

14. The device of claim 1, further comprising a second set of gripping surfaces at about the second axial position and on the opposite side of the needle shield from the first set of gripping surfaces.

15. The device of claim 1, wherein the plastic is colored.

16. The device of claim 1, wherein the needle access first fluid port and the needleless access second fluid port are oriented on opposite sides from each other on the main tubular body.

* * * * *